(12) United States Patent
Burton et al.

(10) Patent No.: US 8,198,407 B1
(45) Date of Patent: Jun. 12, 2012

(54) SEQUENTIAL PROTEIN ISOLATION AND PURIFICATION SCHEMES BY AFFINITY CHROMATOGRAPHY

(75) Inventors: Steven J. Burton, Little Eversden (GB); Baldev Baines, Biggleswade (GB); John Curling, Uppsala (SE); Christopher Bryant, Bourbonnais, IL (US); David John Hammond, Laytonsville, MD (US); Dwun-Hou Chen, Rockville, MD (US); Timothy Keith Hayes, Gaithersburg, MD (US)

(73) Assignees: Prometic Biosciences, Ltd., Freeport, Ballasalla, British Isles (IM); The American National Red Cross, Rockville, MD (US)

( * ) Notice: Subject to any disclaimer, the term of this patent is extended or adjusted under 35 U.S.C. 154(b) by 411 days.

(21) Appl. No.: 11/207,440

(22) Filed: Aug. 19, 2005

Related U.S. Application Data

(60) Provisional application No. 60/602,868, filed on Aug. 20, 2004.

(51) Int. Cl.
*A61K 38/00* (2006.01)
*C12N 5/07* (2010.01)
*C12P 21/04* (2006.01)

(52) U.S. Cl. .......... 530/334; 435/337; 435/69.6

(58) Field of Classification Search .......... None
See application file for complete search history.

(56) References Cited

U.S. PATENT DOCUMENTS

| | | | |
|---|---|---|---|
| 3,842,061 A | 10/1974 | Andersson | |
| 3,943,245 A | 3/1976 | Silverstein | |
| 4,011,067 A | 3/1977 | Carey, Jr. | |
| 4,061,735 A | 12/1977 | Funakoshi et al. | |
| 4,093,606 A | 6/1978 | Coval | |
| 4,093,608 A | 6/1978 | Iga et al. | |
| 4,137,307 A | 1/1979 | Funakoshi et al. | |
| 4,361,652 A | 11/1982 | Uemura et al. | |
| 4,361,653 A | 11/1982 | Watanabe et al. | |
| 4,371,520 A | 2/1983 | Uemura et al. | |
| 4,565,651 A | 1/1986 | Ohmura et al. | |
| 4,822,872 A | 4/1989 | Kameyama et al. | |
| 5,138,034 A | 8/1992 | Uemura et al. | |
| 5,187,155 A | 2/1993 | Fair | |
| 5,576,220 A | 11/1996 | Hudson et al. | |
| 5,985,836 A | 11/1999 | Bastek et al. | |
| 6,037,457 A | 3/2000 | Lord | |
| 6,117,996 A | 9/2000 | Lowe et al. | |
| 6,228,613 B1 | 5/2001 | Fischer et al. | |

FOREIGN PATENT DOCUMENTS

| | | |
|---|---|---|
| CA | 2185617 A1 | 3/1997 |
| EP | 0408029 A1 | 1/1991 |
| EP | 0764658 A1 | 3/1997 |
| JP | 3128398 | 5/1991 |
| JP | 9124508 | 5/1997 |
| JP | 2000506869 | 6/2000 |
| JP | 2003512594 | 4/2003 |
| WO | 0048703 A1 | 8/2000 |

OTHER PUBLICATIONS

Burnouf et al. 2001. Affinity Chromatography in the industrial purification of plasma proteins for therapeutic use. J. Biochem. Biophysi. Methods 49 (2001)575-586.*
Dubin et al. Isolation of nine human plasma proteinase inhibitors by sequential affinity chromatography. Prep Biochem. 1990;20(1):63-74 Abstract.*
Amersham Pharmacia Biotech (see Affinity Chromatography Principles and Methods; Uppsala Sweden, 1999; catalogue No. 18-1002-29.*
Lam et al., *Nature*: 354, 82-84 (1991).
Sproule et.al., *Chromatography*: B, 740, 17-33 (2000).
Cohn et.al., *J. Am. Chem. Soc.*: 68, 459-475 (1946).
Harvey MJ. In: Curling JM (ed) *Methods of Plasma Protein Fractionation*. Academic Press London. pp. 189-200.
Travis, J., and Pannell, R. Behring *Inst. Mitt.* 54: 30-32 (1974).
Deutsch Dale G. and Mertz Edwin T, Science: 170, 1095 (1970).
Fodor et al., *Science*: 251, 767-773 (1991).
Houghten et al., *Nature*: 354:84-86 (1991).
Brenner Sydney and Lerner Richard A., *Proc. Natl. Acad. Sci. USA*: 89:5381-5383 (1992).
Scott Jamie K., and Smith George P., *Science*: 249:386-390 (1990).
Devlin et al., *Science* 249:404-406 (1990).
Christian et al., *J. Mol. Biol.*: 227:711-718 (1992).
Mattheakis et al., *Proc. Natl. Acad. Sci. USA*: 91, 9022-9026 (1994).
Ostresh et al., *Proc. Natl. Acad. Sci. USA*: 91:11138-11142 (1994).
Ecker David J., and Crooke Stanley T., *Bio/Technology*: 13:351-360 (1995).
Bunin et al., *Proc. Natl. Acad. Sci. USA*: 91:4708-4712 (1994).
Simon et al., *Proc. Natl. Acad Sci. USA*: 89:9367-9371 (1992).
Parmley F. Stephan and Smith George P., *Adv. Exp. Med. Biol.* 251:215-218 (1989).
Fowlkes et al., *BioTechniques*: 13:422-427 (1992).
Oldenburg et al., *Proc. Natl. Acad. Sci. USA*: 89:5393-5397 (1992).
Yu et al., *Cell*:76:933-945 (1994).
Devlin et al., Science; 249, 404-406 (1990).
Biancala et al., *Letters in Peptide Science*: 7(291), 297(2000).
MacBeath et al., *Science*, 289, 1760-1763 (2000).
Cook et al., *Tetrahedron Letters*: 35, 6777-6780 (1994).
Nord et al. Ligands selected from combinatorial libraries of protein a for use in affinity capture of apolipoprotein A-1M and Tag DNA polymerase. *J Biotechnol.*: 80, 45-54 (2000).
Pingali et al. Peptides as Affinity Surfaces for Protein Purification. *J. Molec. Recognit*: 9, 426-432.( 1996).
Rodrigo et al. Identification of paraoxonase 3 in rat liver microsomes: purification and biochemcial properties. *Biochem. J.*: 376, 261-268 (2003).

* cited by examiner

*Primary Examiner* — Kagnew H Gebreyesus
(74) *Attorney, Agent, or Firm* — LeClairRyan, a Professional Corporation

(57) ABSTRACT

The invention discloses methods for sequential protein isolation and purification from a biological sample by affinity chromatography. Affinity chromatography is conducted using ligands or ligand support complexes that selectively and specifically bind to proteins in the biological sample. The ligands or ligand support complexes were contacted sequentially in a predetermined order with the biological sample to allow each ligand or ligand-support complex to sequentially bind a protein from the biological sample.

14 Claims, No Drawings

SEQUENTIAL PROTEIN ISOLATION AND PURIFICATION SCHEMES BY AFFINITY CHROMATOGRAPHY

CROSS-REFERENCE TO RELATED APPLICATIONS

This application claims benefit of the Provisional Patent Application Ser. No. 60/602,868, filed Aug. 20, 2004, the entire contents of which are hereby incorporated by reference in their entirety.

I. FIELD OF THE INVENTION

This invention relates to methods for isolation of proteins from biological samples. In particular, the invention relates to methods for recovering highly purified proteins sequentially from biological samples.

II. BACKGROUND OF THE INVENTION

Protein processing and development requires high efficiency processing with the minimum number of steps and the maximum output to achieve the required purity. Protein separation and purification processes present unique challenges due to the variety of proteins, the different nature of possible contaminants and/or impurities associated with each protein preparation, and the large quantity of proteins usually needed for the production of biopharmaceuticals. Conventional purification technologies generally involve a series of purification steps with the objective of isolating a single protein target. With each step, the yield decreases and manufacturing costs increase. Protein separation and purification costs typically represent over 50% of the total manufacturing costs of all therapeutic proteins.

Affinity chromatography is one of the most important separation techniques at the heart of the drug discovery and process development. The more selective the affinity step(s), the greater the efficiency of the entire enterprise, which is a critical requirement in protein fractionation experiments. Affinity chromatography finds a number of practical applications in purification, detection and removal of target molecules from multicomponent streams. Affinity chromatography is based on specific, three-dimensional interactions between target molecules and entities to which they bind (i.e., ligands). Ligands can be isolated or generated for binding in a specific and reversible manner to practically any target molecule. Potential ligands include biological molecules such as proteins, antibodies, peptides and the like, and specifically designed or selected synthetic ligands. Libraries of millions of potential ligands may be generated using combinatorial synthesis techniques, many of which are well known in the art (see, for example, Lam et al., *Nature:* 354, 82-84 (1991)). To aid in separation of target molecules from a sample, ligands can be affixed to a solid support matrix, such as individual particles (e.g., chromatography resin beads) or contiguous supports (e.g., arrays). Ligands immobilized on a solid support matrix can then be employed to purify targets from complex solutions.

Perhaps the greatest success of affinity chromatography at scale has been achieved in the field of biopharmaceutical monoclonal antibody purification. The demand for Protein A resin is more than 10,000 liters annually and increasing at 50% per year, representing a Protein A adsorbent market in excess of $50 Million U.S. in 2002. The use of immunoaffinity chromatography enables the production of both plasma-derived and recombinant coagulation factors VIII and IX as well as other plasma proteins and biopharmaceuticals from natural and recombinant sources.

One of the most powerful forms of modern affinity chromatography for use in downstream processing, however, relies not on ligands derived from natural sources such as antibodies, but on the use of highly stable synthetic affinity ligands. See, for example, Sproule et. al., New Strategy for the Design of Ligands for the Purification of pharmaceutical proteins by affinity chromatography; *J. Chromatography B,* 740, 17-33 (2000). This approach uses customized or designer ligands instead of using off-the-shelf compounds.

Among plasma proteins isolated in the art, albumin and gammaglobulin have particularly been targeted for medicinal purposes. Procedures commonly employed to isolate these proteins from plasma were based on the cold ethanol precipitation process developed by E. J. Cohn and co-workers during the 1940's. See Cohn et. al., Preparation and Properties of Serum and Plasma Proteins. IV. A System for the Separation into Fractions of the Protein and Lipoprotein Components of Biological Tissues and Fluids; *J. Am. Chem. Soc.,* 68, 459-475 (1946). This process was originally developed to produce albumin in high yield but was not designed to isolate and purify the diverse array of proteins now produced from plasma. In particular the yields of minor plasma protein components by these techniques are invariably so low that the techniques are inevitably inefficient in terms of the overall fractionation yield. See, for example, U.S. Pat. No. 5,138,034 to Uemura et al.

The application of affinity chromatography to the purification of serum albumin is known in the art, see Harvey M J. In: Curling J M (ed) *Methods of Plasma Protein Fractionation.* Academic Press London. pp 189-200. The first reported separation of proteins from plasma dated about 30 years ago and concerned the depletion of human serum .albumin (HSA) by chromatography from plasma to enable identification and purification of low concentration proteins. Travis, J., and Pannell, R. Behring *Inst. Mitt.* 54: 30-32 (1974). This work was carried out using a Procion Blue dextran-Sepharose® conjugate and identified an initial problem with dye-affinity chromatography, namely the leakage of the dye into the eluate. The authors were interested in the isolation of alpha 1-antitrypsin from plasma and described the difficult separation of this protein from albumin at high ionic strength where any non-specific ion exchange binding is at a minimum.

The isolation of various other proteins from plasma is also reported. For example, the prior art methods described isolation and purification plasma protein Factor VIII and fibronectin fractions, see, for example, U.S. Pat. Nos. 4,822,872; 4,093,608; and 4,565,651. Methods for isolation and purification of antithrombin-III are disclosed in, for example, U.S. Pat. No. 3,842,061. Methods for isolation and purification of plasminogen are disclosed in, for example, *Science:* 170, 1095 (1970), U.S. Pat. Nos. 4,361,652 and 4,361,653. Methods for isolation and purification of immunoglobulins are described, for example, in U.S. Pat. Nos. 4,371,520 and 4,093,606. Methods for isolation and purification of hepataglobulin are described in, for example, U.S. Pat. Nos. 4,061,735 and 4,137,307. These methods, however, lack the specificity and selectivity required for isolation of proteins used in the production of multiple biopharmaceutical agents from the same starting material, e.g., human plasma.

Although the processes for isolating proteins from biological samples have provided some improvement in product quality, in terms of enhanced specific activity and purity, and also in yield or recovery, there still remains a need for further process improvement to obtain a protein concentrate in high yield and high purity with minimization of the reduction in the specific activity of the isolated proteins often associated with prior art processes. This is particularly true in situations where multiple protein targets are isolated simultaneously from a common source. This invention solves these and other long felt needs by providing methods utilizing affinity chromatography techniques to isolate and purify various proteins efficiently from biological materials, and particularly from plasma, by combining adsorption processes in pre-determined and defined sequences.

III. SUMMARY OF THE INVENTION

The invention, as disclosed and described herein, provides methods for sequential protein isolation and purification from biological samples. The methods comprise (i) providing a biological sample, (ii) providing two or more ligands each of which selectively and specifically binds to a target protein from the biological sample, wherein each of the ligands is optionally attached to a support to form two or more ligand-support complexes, (iii) contacting sequentially two or more ligands or ligand support complexes in a predetermined order with the biological sample to allow each ligand or ligand support complex to sequentially bind the target protein from the biological sample, wherein the biological sample is not processed through a pre-conditioning step prior to contacting, (iv) eluting the target protein bound to each of the two or more ligands or ligand support complexes, and (v) isolating the target protein sequentially from the biological sample. The pre-conditioning step comprises various processes such as, for example, alcohol precipitation, cryoprecipitation, removal of lipids and/or lipid proteins, euglobulin precipitation, or a combination thereof, among others.

In one embodiment, the biological sample is plasma and the target protein comprises fibrinogen (Fg), alpha-1 proteinase inhibitor (A1PI), apolipoprotein A1 (ApoA1), immunoglobulins (IgG), paraoxonase (PON), coagulation factors, Von Willebrand factor (vWF), Factor VIII (FVIII), human serum albumin (HSA), plasminogen (Pg), or any combination thereof.

In another embodiment, the biological sample comprises an in vitro fermentation or cell culture or a tissue or fluid extracted from a transgenic animal or plant, and the proteins are recombinant proteins.

In yet another embodiment, the activity of paraoxonase is substantially maintained in the biological sample during the protein isolation.

In one embodiment, vWF/FVIII is isolated from the plasma prior to other proteins, or after the other proteins.

In another embodiment, apolipoprotein A1 is isolated from the plasma after other proteins.

In yet another embodiment, albumin is isolated from the plasma prior to IgG or after IgG.

In another embodiment, plasminogen is isolated from the plasma prior to fibrinogen.

In yet another embodiment, the predetermined order of contacting the two or more ligands with the biological sample results in the sequential binding of vWF/FVIII, Pg, Fg, ApoA1/PON, IgG, HSA, and A1PI in the recited order.

In another embodiment, the predetermined order of contacting the two or more ligands with the biological sample results in the sequential binding of vWF/FVIII, ApoA1/PON, Pg, Fg, IgG, HSA, and A1PI in the recited order.

In a further embodiment, the predetermined order of contacting the two or more ligands with the biological sample results in the sequential binding of vWF/FVIII, IgG, HSA, and A1PI in the recited order.

The ligands of the invention comprise polypeptide or nucleic acid-based molecules, antibodies or antigen-binding fragments, non-polypeptide or nucleotide-based molecules, carbohydrate mimetics, peptidomimetics, small molecules, inorganic materials, dyes, carbohydrates, lipids, or any combination thereof.

In one embodiment, the ligands are peptides comprising of about 1 to about 15 amino acids.

In another embodiment, the ligands and/or ligand support complexes comprise synthetic affinity ligands such as Mimetic Blue® ligands, MAbsorbent® ligands, ProMetic PBL 112-80, ProMetic PBL 112-81, ProMetic PBL 112-82, and ProMetic PBL 112-83.

The support comprises a synthetic material, a natural material, or both. Examples of supports include agarose, polyacrylamide, dextran, cellulose, polysaccharide, nitrocellulose, silica, alumina, aluminum oxide, titania, titanium oxide, zirconia, styrene, polyvinyldifluoride nylon, copolymer of styrene and divinylbenzene, polymethacrylate ester, hydroxyethylmethacrylate, acrylic, polyvinylalcohol, polyethyleneglycol, derivatized azlactone polymer or copolymer, glass, cellulose, agarose, derivatives of any of the foregoing, and combinations of any of the foregoing.

In a preferred embodiment, the support is a polysaccharide or resin bead.

In another aspect, the invention provides a preparation comprising a substantially pure plasma protein produced by the sequential protein isolation of the invention.

In one embodiment, the plasma is substantially purified with a purity of at least 70%.

In another embodiment, the preparation is substantially purified, free from any immunoadsorbent-caused impurities, and has been subjected to at least one pathogen inactivation step.

In yet another embodiment, the biological sample is treated by a buffering agent prior to the step of contacting in order to further conserve concentration and activity of one or more target agents in the biological sample.

In another aspect, the preparation is formulated as a pharmaceutical composition. These and other aspects and embodiments of the invention are disclosed in detail herein.

IV. DETAILED DESCRIPTION OF THE INVENTION

Methods for efficient isolation and purification of proteins from biological samples are disclosed herein. In particular, the present invention discloses methods of sequential protein purification from plasma using affinity chromatography. The sequential protein purification methods of the present invention use two or more ligands, each ligand is optionally attached to a support to form a ligand-support complex. Each ligand or ligand support complex selectively and specifically binds to a target plasma protein in a predetermined order to allow each ligand or ligand support complex to sequentially bind a target protein from plasma.

The sequential protein isolation and purification methods of the invention are highly specific and do not require specific pre-conditioning of plasma, as routinely used in the prior art, prior to contacting with the ligand. Such pre-conditioning step does not include buffering or general filtration. Pre-conditioning step within the scope of the invention include, for example, methods and processes such as alcohol precipitation, cryoprecipitation, removal of lipids and/or lipid proteins, euglobulin precipitation, or a combination thereof, among others. It is intended herein that the aforementioned pre-conditioning steps are specifically excluded from the invention claimed. The plasma protein purification methods of the present invention are highly valuable in the production of biopharmaceuticals because of their ability to produce substantially pure and highly active plasma proteins efficiently and rapidly. The methods of the present invention are also useful in a variety of other applications including prognostic, diagnostic, and/or detection of abnormalities.

1. DEFINITIONS

The definitions used in this application are for illustrative purposes and do not limit the scope of the invention.

As used herein, "sample" includes any sample containing a target protein that can be isolated and purified by the method of the invention. Samples may be obtained from any source that potentially contains a target protein. Such sources include animals, plants, soil, air, water, fungi, bacteria, and viruses, among others. Animal samples are obtained, for example from tissue biopsy, blood, hair, buccal scrapes, plasma, serum, skin, ascites, plural effusion, thoracentesis fluid, spinal fluid, lymph fluid, bone marrow, respiratory fluid, intestinal fluid, genital fluid, stool, urine, sputum, tears, saliva, tumors, organs, tissues, samples of in vitro cell culture constituents, fetal cells, placenta cells or amniotic cells and/or fluid, among others.

As used herein, "cell culture" includes any prokaryotic or eukaryotic culture such as, for example, bacterial, yeast and other microbiological cell culture, mammalian cell culture, plant cell culture, and insect culture, fermentation broths and other cell culture used for the production and delivery of biopharmaceuticals and the preparation of therapeutics.

As used herein, "plasma" refers to liquid blood components and includes plasma derivatives, and plasma-containing compositions.

As used herein, "attachment" is broadly defined within the scope of the invention and includes any type of physical, chemical, or biological bonding processes between two entities and includes, for example and not by way of limitation, absorption, adsorption, covalent bonding, ion exchange, hydrophobic, hydrogen bonding, dipole, quadrupole or affinity interaction, formation of charged species, the attachment of affinity ligands (e.g., including peptides, oligonucleotides, proteins, spacer arms, hydrophobic moieties, and fluorinated materials), among others.

As used herein, "ligands" are defined broadly within the scope of the invention and include chemical, or biological entities that bind to a target protein. Ligands are compounds, molecules, cells, and cell constituents that bind to a target protein and can be isolated from natural or synthetically produced materials. Ligands can be endogenous or exogenous to a prokaryote or eukaryote. Ligands include peptides, polypeptides, peptidomimetics, small molecules, dyes, triazine containing compounds, antibody or antigen-binding fragments, nucleic acid-based molecules, non-polypeptide or nucleotide-based molecules, carbohydrates, carbohydrate mimetics, lipids, inorganic materials, inhibitors, substrates or any combination thereof.

As used herein, "substantially purified" or "substantially free," refers to proteins that are removed from their natural environment and are isolated or separated, and are at least about 70% free, preferably about 85% free, more preferably about 95%, and most preferably about 99% or more free from other components with which they are naturally associated.

As used herein "polypeptide-based molecules" include any proteins, polypeptides or peptide fragments, natural peptides, recombinant peptides, synthetic peptides, biologically active fragments, substantially homologous polypeptides, oligopeptides, homodimers, heterodimers, variants of the polypeptides, modified polypeptides, derivatives, analogs, fusion proteins, agonists, antagonists, and antibodies, among others.

As used herein "small molecules" include, but are not limited to, carbohydrates, carbohydrate-mimetics, peptidomimetics, organic or inorganic compounds (i.e, including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other chemically acceptable forms of such compounds.

As used herein, the term "pathogen" is intended to mean any replicable agent that can be found in a biological sample such as a blood sample or infect an organism. Such pathogens include the various viruses, bacteria, protozoa, and parasites known to those of skill in the art to generally be found in or infect whole blood or blood components and other pathogenic contaminants not yet known. Illustrative examples of such pathogens include, but are not limited to, bacteria, such as *Streptococcus* species, *Escherichia* species and *Bacillus* species; viruses, such as human immunodeficiency viruses and other retroviruses, herpes viruses, paramyxoviruses, cytomegaloviruses, hepatitis viruses (including hepatitis A, hepatitis B, and hepatitis C), pox viruses and toga viruses; and parasites, such as malarial parasites, including *Plasmodium* species, and trypanosomal parasites.

Other terms used in the field of protein purification as used herein will be generally understood by one of ordinary skill in the applicable art.

In one embodiment, the invention provides methods for extraction of specific plasma proteins from plasma. These methods utilize chromatography resins to which ligands, selective and specific for two or more plasma proteins are attached thereto. The resins are brought in to contact with plasma, which contact results in the selective binding of the target protein with the ligand. The target protein can then be eluted with high recovery and purity. Thus, in accordance with the method of the present invention, plasma can be efficiently fractionated into various component plasma proteins. Preferred sequences for the extraction and subsequent isolation of specific plasma proteins are disclosed herein.

Plasma proteins within the scope of the invention include any and all of more than 10,000 different proteins occurring in plasma, including, for example and not by way of limitation, butyrylcholinesterase (BChE), blood coagulation factors (e.g., fibrinogen, factor II, factor V, factor VII, factor VIII, factor IX, factor X, factor XI and factor XII), fibronectin, prothrombin, protein C, plasminogen, antithrombin-III, haptoglobin, transferrin, albumin, alpha 1 proteinase inhibitor, apolipoprotein A1 (also known as Apo-A1 lipoprotein), immunoglobulins, paraoxonase, Von Willebrand factor (vWF), all of which are naturally found in the plasma of an organism in a non-diseased state.

Alternatively, the plasma protein within the scope of the invention is present in plasma associated with a diseased state, which may or may not be found in the plasma of a healthy subject. Also encompassed within the scope of the invention are the plasma proteins that are present in plasma as a result of the administration of an agent, e.g., a drug. In this regard, the plasma protein can be an infectious PrPsc prion protein.

1. Ligands

The method of protein purification of the invention utilizes two or more ligands that are attached to a support system. The ligands may comprise one or more functional groups to provide ionic, hydrophobic, hydrogen-bonding or Van der Waal's interactions with corresponding groups on the biomolecule to be separated. Suitable ligands for the inventive method include synthetic chemical compounds that are produced, for example, by way of direct synthesis, or diversity libraries, such as random or combinatorial peptide or non-peptide libraries. Other libraries known in the art include chemically synthesized libraries, recombinant libraries (e.g., phage display libraries), and in vitro translation-based libraries. The libraries can be screened for molecules that specifically bind to a target protein of the invention.

Examples of chemically synthesized libraries are described, for example, in Fodor et al., *Science* 251:767-773 (1991); Houghten et al., *Nature* 354:84-86 (1991); Brenner and Lerner, *Proc. Natl. Acad. Sci. USA* 89:5381-5383 (1992), and U.S. Pat. No. 6,117,996 among others. Examples of phage display libraries are described, for example, in Scott and Smith, *Science* 249:386-390 (1990); Devlin et al., *Science* 249:404-406 (1990); and Christian et al., *J. Mol. Biol.* 227:711-718 (1992), among others. In vitro translation-based libraries are described, for example, in Mattheakis et al., *Proc. Natl. Acad. Sci. USA* 91:9022-9026 (1994), among others.

In one embodiment, the ligand of the invention is a peptide essentially consisting of about 3 to about 5, 8, 10, 15, or 30 amino acids or more. The amino acids are D and/or L amino acids. The peptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules.

In peptide libraries, the number of discrete peptides of differing sequence increases dramatically with the number of coupling reactions performed, the size of the peptide, and the number of distinct amino acids utilized. For example, the random incorporation of 19 amino acids into pentapeptides produces up to 2,476,099 ($19^5$) individual peptides of differing sequence (Lam et al., supra). Combinatorial methods allow generation of libraries of ligands directly on a support. Typically, the ligands are synthesized on particles of support such that multiple copies of a single ligand are synthesized on each particle (e.g., bead), although this is not required in the context of the invention.

Another example of a library that can be used, in which the amide functionalities in peptides have been permethylated to generate a chemically transformed combinatorial library, is described by Ostresh et al., *Proc. Natl. Acad. Sci. USA* 91:11138-11142 (1994).

Non-peptide libraries can be classified broadly into two types: decorated monomers and oligomers. Decorated monomer libraries employ a relatively simple scaffold structure upon which a variety of functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, and peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Other non-peptide libraries that are useful in the present invention are, for example, libraries described by Ecker and Crooke, *Bio/Technology* 13:351-360 (1995). These libraries use compounds such as, for example, benzodiazepines, (see, e.g., Bunin et al., *Proc. Natl. Acad. Sci. USA* 91:4708-4712 (1994)) can be adapted for use. Additionally, peptoid libraries (e.g., Simon et al., *Proc. Natl. Acad. Sci. USA* 89:9367-9371 (1992)) can also be used. Other compounds used in peptide libraries include hydantoins, piperazinediones, biphenyls, sugar analogs, beta-mercaptoketones, arylacetic acids, acylpiperidines, benzopyrans, cubanes, xanthines, aminimides, and oxazolones, among others.

Screening the libraries can be accomplished by any of a variety of commonly known methods. See, e.g., the following references, which disclose screening of peptide libraries: Parmley and Smith, *Adv. Exp. Med. Biol.* 251:215-218 (1989); Scott and Smith, id.; Fowlkes et al., *BioTechniques* 13:422-427 (1992); Oldenburg et al., *Proc. Natl. Acad. Sci. USA* 89:5393-5397 (1992); and Yu et al., *Cell* 76:933-945 (1994), among others. Screening to identify a molecule that binds a target protein can also be carried out by contacting the library members with the target protein immobilized on a solid phase and harvesting those library members that bind to the protein of interest. Examples of such screening methods, termed "panning" techniques are described by way of example in Fowlkes et al., id.

Preferably, the ligands of the invention are designed by modeling and combinatorial chemistry and include synthetic/biomimetic ligands that can be symmetrical or asymmetrical, single or branched molecules. The ligands preferably are alkali resistant and withstand normal alkali regeneration and sanitization procedures. The ligands of the invention have very low leakage, are safe and possess high capacity of binding and specificity to the target protein.

Preferred ligands or ligands and support systems used within the scope of the invention include, by way of example and not limitation, Mimetic Blue® ligands (for HSA column), and the resin is designated Mimetic Blue® SAHL P6XL; MAbsorbent® ligands (for binding IgG), and the adsorbent designated MAbsorbent® A2P; ProMetic PBL 112-80 adsorbent for A1PI; ProMetic PBL 112-81 adsorbent for fibrinogen; ProMetic PBL 112-82 adsorbent for plasmiogen; ProMetic PBL 112-83 adsorbent for vWF/FactorVIII; ECH-Lys-Sepharose FF. Lot#243526; SAHL P6XL-Resin; and peptide ligand resins including ARQFDF (SEQ ID NO: 1). The aforementioned adsorbents use Purabead 6XL (cross-linked agarose) as the support matrix. Purabead 6 or 6XL support matrices do not adsorb these proteins on their own.

2. Support

In one embodiment of the inventive method, the ligand is attached to a support. The term "support" as used herein refers to any support matrix, such as those solid supports known in the art, which serve to immobilize the ligand. A support or support matrix is any solid or liquid substance, porous or non-porous, two-dimensional or three-dimensional to which a ligand may be attached and which provides a convenient means of separating the ligand from solutes in a contacting solution. Preferably, the support is inert following ligand attachment such that covalent reaction with the target is minimized.

Also included within the scope of the invention is the use of spacer arms for coupling ligands to the support. Spacer arms can take on a wide variety of different forms, including but not limited to, hydroxylated materials like polyethyleneglycols, polyethylene oxides, linear or branched alkanes, diamines, glycols, aromatic rings, and carbohydrates or any combination thereof among others.

In one embodiment, the support matrix comprises porous particles that are capable of adsorption or absorption of the target agent. The particles are optionally coated with one or more materials to modify the surface properties of the support matrix, which materials are non-swellable or swellable in organic fluids or aqueous fluids and are substantially insoluble in water or fluids.

A preferred support matrix used with the sequential protein purification scheme of the present invention is a porous particle. Porous particles for adsorption separations are available in a large variety of different materials, including silica, glass, cellulose, agarose, and a wide variety of different polymers, including polystyrene polymethylmethacrylate, polyacrylamide, agarose, hydrogel, acrylic resins and other types of gels used for electrophoresis. Many of the porous adsorption particles such as silica, glass and polymers can be dried and have interconnected pores with surface areas in the range of about 1-2 $m^2$/g of dried particles to over 300 $m^2$/g of dried particles. Other types of particles are cross-linked hydrogels.

Particularly preferred support matrices are agarose and polyhydroxylated methacrylate resin. Various beaded agarose gels and polymer resins are commercially available. These supports may be purchased with ligands pre-attached or alternatively, the ligands can be indirectly attached or directly immobilized on the support using standard methods (see, for example, Harlow and Lane, Antibodies, Cold Spring Harbor Laboratory, Cold Spring Harbor, N.Y. (1988); Biancala et al., *Letters in Peptide Science,* 7(291), 297 (2000); MacBeath et al., *Science,* 289, 1760-1763 (2000); Cass et al., ed., *Proceedings of the Thirteenth American Peptide Symposium.* Leiden, Escom, 975-979 (1994); U.S. Pat. No. 5,576, 220; Cook et al., *Tetrahedron Letters;* 35, 6777-6780 (1994); and Fodor et al., supra. In one embodiment, the ligand(s) are synthesized on the surface of the support, which is advantageous in generating peptide libraries. The ligand(s) can be chemically conjugated to the support or can be attached via linkers, such as streptavidin, beta alanine, glycine, polymers containing glycine-serine, short chain hydrocarbons of the formula —$(CH_2)$, polyethylene glycol, epsilon amino caproic acid, and linkers comprising —$O(CH_2)n$, wherein n is 1-30.

3. Binding and Elution of Target Proteins

Binding of target protein or target biomolecule to the ligand or ligand-support complex is normally performed by contacting the ligand or ligand-support complex with an aqueous solution containing the targets. This may be achieved in a variety of ways including but not limited to, passage of the target containing solution through a packed bed or column of the ligand-support complex, or batch adsorption in a stirred tank or slurry. Preferably, the target protein is captured by passage of the aqueous solution through a chromatography column using a pump to control the flow rate. Ideally binding of the protein target should be performed in such a manner that prior adjustment of the solution is not required and the target containing solution is applied directly to the ligand-support complex. However, where required for binding, the properties of the target containing solution may be adjusted by, for example, dilution, changes of pH, ionic strength or polarity, temperature changes, and the addition of soluble agents including but not limited to buffer salts, inorganic salts, organic salts, chelating compounds, thiols, detergents, surfactants, organic solvents, alcohols, glycols, chaotropic agents, metal ions or any combination thereof.

To recover the target protein from the ligand or the ligand-support complex, the ligand or the ligand support complex can be contacted with a solution (e.g., a "transfer solution" or "elution buffer") that promotes dissociation of the target protein from the ligand or the ligand-support complex. The transfer solution can be selected from buffers of various salt concentrations, pH, or denaturation capability, organic solvents, polarity modifying agents such as alcohols and deionized water. Alternatively, or in addition, an electric gradient or temperature change can dissociate the target protein from the protein-ligand-support complex. Transfer solutions also can comprise ligands (different from the ligand of the protein-ligand-support complex), cofactors for the target protein, enantiomeric specific molecules, and the like. The use of different transfer solutions allows investigation of elution conditions or transfer of a specific target protein. The dissociation and transfer conditions employed in the inventive method are selected to minimize disruption of the ligand and of the target protein. In other words, the elution and transfer conditions should not release the ligand from the support or denature the target protein, unless this is desired.

In one embodiment, the target protein is detected and identified on the protein-ligand support prior to elution. Detecting and identification of the target protein on protein-ligand support can comprise performing a binding assay. A binding assay typically involves contacting the protein-ligand support, with a moiety known to bind to a substrate. Binding moieties for use in binding assays include, for instance, antibodies or antigen-binding fragments thereof, proteins, or oligonucleotides. Preferably, the protein-ligand support is contacted with an antibody or an antigen-binding fragment thereof that binds the target protein (or chemical or biological byproduct of the target protein or a fragment thereof). The binding moiety preferably is labeled with a detectable tag such as, for instance, a radioisotope, a chromophore, or a fluorescent tag. In such a binding assay, a signal emitted by the detectable tag is detected, thereby signaling the presence of the target protein. Once the presence of the target protein on the protein-ligand support is elucidated, the protein can be isolated.

Binding assays for detection of a target are further described in, for example, Harlow and Lane, supra; Sambrook et al., *Molecular Cloning*, A Laboratory Manual, 2d edition, Cold Spring Harbor Press, Cold Spring Harbor, N.Y. (1989); and Haugland, *Handbook of Fluorescent Probes and Research Chemicals* (9th ed.), Molecular Probes, Eugene, Oreg. (2002). Optionally, the inventive method can further comprise a washing step to remove excess, unbound binding moieties or markers prior to detection.

Alternatively, the inventive method can comprise performing an enzyme activity assay to characterize a target protein on the basis of biological activity. An enzyme substrate is applied to the protein-ligand support which allows for enzymatic modification of the substrate by the target protein to form a product. The product is then detected, thereby identifying the presence of the target protein in the sample.

The binding and elution of target proteins can be measured by any suitable method, many of which exist and whose performance and suitability for a particular purpose will be known to a person skilled in the art.

4. Methods of Use

The present invention as described herein provides methods for sequential isolation of proteins from biological samples, which methods produce highly active and substantially purified proteins. The methods of the invention are highly sensitive and capable of separating minute amounts of target proteins from a sample. The sequential protein purification methods of the invention are useful in a variety of applications including prognostic, diagnostic, detection, purification, separation, processing of expressed in vitro gene products, and production of biopharmaceuticals. The purification and extraction techniques of the invention offer advantages over conventional purification techniques by reducing the number of purification steps, improving yields, increasing purity, and overcoming limitations associated with the traditional methods.

In particular, the methods of the present invention optimize the protein purification process and improve the manufacturing process of biopharmaceuticals by increasing efficiency and purity. Biopharmaceuticals are drugs that comprise proteins, peptides or other complex polynucleotides or protein based macromolecules (collectively "gene products"). Their manufacturing process involves the recovery of the desired gene product from its host biomass, such as plasma or non-human biological sources (e.g., recombinant or non-recombinant cell cultures, milk of transgenic animals or other recombinant or non-recombinant sources). Recovering commercially viable yields of a desired protein from a biomass is challenging since the latter contains unwanted host proteins, nucleic acid molecules and other naturally occurring chemical entities.

In one embodiment, the methods of the present invention are used for the isolation of proteins from whole blood, red blood cell concentrates, platelet concentrates, plasma, plasma derivatives, leukocytes, leukodepleted blood, mammalian cell culture, fermentation broths and other media used for the production and delivery of biopharmaceuticals and the preparation of therapeutics.

In a preferred embodiment, the methods of the present invention isolate highly active plasma proteins sequentially from a plasma sample. Multiple proteins can be separated from the sample concomitantly and rapidly by the methods of the present invention from any stream in the plasma processing industry aimed at the production of therapeutic and/or pharmaceutical products. An example of the order of isolation of plasma protein in disclosed in Table 1 below.

TABLE 1

Plasma Protein Purification Scheme

| Full Cascade | Cascade 1 | Abbreviated Cascade | Inverted Cascade |
|---|---|---|---|
| vWF/FVIII | vWF/FVIII | | vWF/FVIII |
| PON | | | |
| Pg | Pg | | |
| Fg | Fg | | |
| IgG | IgG | IgG | HAS |
| HSA | UF/DF | HAS | IgG |
| UF/DF | HSA | UF/DF | UF/DF |
| A1PI | UF/DF | A1PI | A1PI |
| | A1PI | | |

The isolated plasma protein is "substantially purified," having a purity of about 70%, preferably about 85%, more preferably about 95%, and most preferably about 99% or more. It is intended herein that by recitation of such specific purification values, the values recited also include all those specific integer amounts between the recited values. For example, about 85% is intended to also encompass 80%, 81%, 82%, 83%, and 84%, without actually reciting each specific degree of substantial purification therein.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Definition of Linear Cascade Sequence Scenarios 1-7

The linear cascade was composed of five affinity chromatography columns: Albumin (HSA), Fibrinogen (Fg), IgG, Plasminogen (Pg), and PON1/ApoA1. Initially, these columns were run successively in four different sequences to determine the optimal sequence for the linear cascade. In order to simplify the in-process sample analysis, only non-diluted flow-through was collected as the load for the next column in the sequence. Specifically, this aided in keeping the concentration of background proteins constant throughout the experiment. It also simplified the comparison of output versus input on each column. Samples of the load and each flow-through were assayed to monitor the recovery of the target and non-target proteins in the flow-through. These values were used to monitor each column to determine its ability to capture its target protein with minimal retention of downstream target proteins. The sequence that best fit this criterion was used as the Linear Cascade Sequence (LCS). Once the analytical data from the first runs became available, three additional sequences were tested, and the A1PI column was added in for Scenarios 6 and 7.

Materials and Equipment

The following resins were used in the cascades packed in Pharmacia XK 50 columns (20 or 30 m length):

Plasminogen column: Pharmacia ECH-Lys-Sepharose FF. Lot#243526.

Fibrinogen column: ProMetic Purabead, (2 columns in series) Lot#CG1251 and Lot#CG1252.

IgG column: ProMetic MAbsorbent A2P, Lot#FA0582-Z.

HSA column: ProMetic Mimetic Blue SAHL P6XL Batch # FA0500Z.

PON1/ApoA1 column: Peptide International, Toyopearl WWLHAN Lot#217772.

A1PI column: ProMetic 12/330 P6XL Resin Batch # CG 1255.

All chromatography was performed using the AKTA Explorer 100 chromatography system with 950 fraction collectors (Amersham Biosciences). Ultrafiltration (UF)/diafiltration (DF) was performed with the Sartorius Sartocon Slice 200 Ultrafiltration System using two 200 $cm^2$ Hydrosart cellulose acetate membranes (10 kD molecular weight cut off).

Methods

For each run, the load for the first column was pooled human plasma+50 mM Tris, pH 7.5 filtered to 0.2 μm. The flow-through for each column was collected in fractions and pooled based on the UV absorbance ($A_{280}$) profile of the chromatogram. This pool was used as the load material for the next column in the sequence. If the next column was to be run the following day, the flow-through was sterile filtered (0.2

μm vacuum filter) and stored at room temperature. In Scenarios 6 and 7, UF/DF was used to reduce the volume and perform a buffer exchange on the pooled flow-through as indicated in Table 2 below. This was required to bring the A1PI load material into the A1PI column running buffer (15 mM sodium phosphate, pH 6.1).

TABLE 2

Column Sequences

| | |
|---|---|
| Scenario #1 | Pg → Fg → IgG → HSA → ApoA-1/PON1 |
| Scenario #2 | IgG → Fg → Pg → HSA → ApoA-1/PON1 |
| Scenario #3 | Pg → Fg → HSA → IgG |
| Scenario #4 | Pg → Fg → ApoA-1/PON1 → HSA → IgG |
| Scenario #5 | ApoA1/PON1 → Pg → Fg → HSA → IgG |
| Scenario #6 | Pg → Fg → ApoA1/PON1 → HSA → UF/DF → IgG → A1PI. |
| Scenario #7 | ApoA1/PON1 → Pg → Fg → HSA → IgG → UF/DF → A1PI |

Results

Step yield tables and graphs are shown below for each scenario. N/A means that the data was not available. <LOD means that the level of protein was below the limit of detection for that particular assay.

TABLE 3

Percent Step Yields for Scenario #1

| | Pg | Fg | IgG | HSA | ApoA1 |
|---|---|---|---|---|---|
| Pg FT | 4.6% | 98.9% | 96.0% | 101.7% | 91.8% |
| Fg FT | | 0.0% | 94.5% | 90.8% | 84.9% |
| IgG FT | | | 3.0% | 78.3% | 84.5% |
| HSA FT | | | | 2.8% | 81.9% |
| PON1 FT | | | | | N/A |

Table 3 summarizes the results of scenario #1

TABLE 4

Percent Step Yields for Scenario #2

| | IgG | Fg | Pg | HSA | ApoA1 | A1 PI |
|---|---|---|---|---|---|---|
| IgG FT | 2.19% | 2.97% | 3.51% | 81.81% | 2.09% | 77.19% |
| Fg FT | | <LOD | <LOD | 93.29% | <LOD | 89.01% |
| Pg FT | | | <LOD | 112.26% | <LOD | 113.34% |
| HSA FT | | | | 1.00% | <LOD | 88.42% |
| PON1 FT | | | | | <LOD | 1.00% |

Table 4 summarizes the results of scenario #2.

TABLE 5

Percent Step Yields for Scenario #3

| | Pg | Fg | has | IgG | ApoA1 | A1 PI |
|---|---|---|---|---|---|---|
| Pg FT | 3.47% | 90.06% | 86.14% | 89.61% | 86.05% | 85.68% |
| Fg FT | | 1.01% | 81.67% | 70.80% | 70.20% | 75.03% |
| HSA FT | | | 22.74% | 74.39% | 73.74% | 61.34% |
| IgG FT | | | | 6.82% | 1.37% | 67.40% |

Table 5 summarizes the results of scenario #3.

TABLE 6

Percent Step Yields for Scenario #4

| | Pg | Fg | ApoA1 | HSA | IgG | A1 PI |
|---|---|---|---|---|---|---|
| Pg FT | 2.0% | 96.0% | 90.0% | 94.0% | 93.0% | 93% |
| Fg FT | | 4.0% | 83.0% | 83.0% | 86.0% | 84% |
| ApoA1 FT | | | 1.0% | 99.0% | 83.0% | 79% |
| HSA FT | | | | 1.0% | 89.0% | 101% |
| IgG FT | | | | | 0.0% | 79% |

Table 6 summarizes the results of scenario #4.

TABLE 7

Percent Step Yields for Scenario #5

| | ApoA1 | Pg | Fg | HSA | IgG |
|---|---|---|---|---|---|
| PON1 FT | 8.20% | 78.0%* | N/A | 89.10% | 93.10% |
| Pg FT | | 0.10% | 62.00% | 87.70% | 86.60% |
| Fg FT | | | 2.50% | 73.80% | 72.20% |
| HSA FT | | | | 5.00% | 60.80% |
| IgG FT | | | | | 0.70% |

*based on activity assay, Nephelometry data not available

Table 7 summarizes the results of scenario #5.

TABLE 8

Percent Step Yields for Scenario #6

| | Pg | Fg | ApoA1 | HSA | A1 PI | IgG |
|---|---|---|---|---|---|---|
| Pg FT | 2.00% | 91.48% | 82.09% | 89.67% | 81.29% | 89.06% |
| Fg FT | | 22.90% | 75.10% | 104.50% | 103.12% | 106.60% |
| PON1 FT | | | <LOD | 94.13% | 88.76% | 99.26% |
| HSA FT | | | | 1.89% | 88.57% | 73.34% |
| A1PI FT | | | | | <LOD | 60.52% |
| IgG FT | | | | | <LOD | <LOD |

Table 8 summarizes the results of scenario #6

TABLE 9

Percent Step Yields for Scenario #7

| | ApoA1 | Pg | Fg | HSA FT | IgG FT | A1 PI |
|---|---|---|---|---|---|---|
| ApoA1 | 25.4% | 73.6% | 78.5% | 75.9% | 76.0% | 63.7% |
| Pg | | <2.6% | 85.5% | 88.7% | 87.6% | 85.4% |
| Fg | | | 9.5% | 71.4% | 72.8% | 57.9% |
| HSA FT | | | | 3.7% | 42.1% | 58.7% |
| IgG FT | | | | | <0.2% | 54.8% |
| A1PI | | | | | | <9.2% |

Table 9 summarizes the results of scenario #7.

Conclusions

In the run preceding Scenario #1 (same sequence as that of Scenario #1), the starting material was filtered plasma without any added buffering system. As the plasma was loaded on the column, there was a substantial spike in the pH of the flow-through. As a result of this observation, 1M Tris buffer, pH 7.5 was added to the plasma to a final concentration of 50 mM Tris before being loaded on to the first column. See, Example 3 below for a summary of the buffer selection process. The seven scenarios demonstrated the feasibility of running a linear cascade of affinity columns as an effective process for purifying plasma proteins. The data was analyzed and the sequence was selected based on the following observations. In Scenario 1, the recovery of downstream target proteins remained fairly high throughout the run. In Scenario 2, the IgG column almost entirely depleted the feed stream of Plasminogen, Fibrinogen, and ApoA1. Again in Scenario 3, the IgG column captured ApoA1. On the basis of this observation, it was determined that the PON1, Pg, and Fg columns had to be placed before the IgG column in the sequence.

The following points were taken into consideration when deciding the order of the chromatography steps in the linear cascade according to this experiment:

Capture steps for PON1, Pg, and Fg should be placed before IgG.

Since Albumin and citrate will interfere with the A1PI chromatography, the A1PI column should be placed after the Albumin column. The flow-through requires a UF/DF process step for a buffer exchange, before the A1PI column.

IgG should be placed before Albumin to avoid losses of IgG.

Therefore, the linear cascade sequence in this experiment was chosen to be:

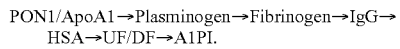

PON1/ApoA1→Plasminogen→Fibrinogen→IgG→ HSA→UF/DF→A1PI.

It should be noted that in another experiment the PON1/ApoA1 column was removed from the current cascade sequence and that vWF/FVIII was inserted prior to Plasminogen when the resin becomes available.

Example 2

Affinity Capture of Plasma Proteins

The following column sequence used in this experiment:

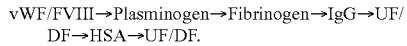

vWF/FVIII→Plasminogen→Fibrinogen→IgG→UF/ DF→HSA→UF/DF.

Plasma Preparation Four liter of frozen pooled plasma was obtained from −20° C. storage. Plasma pool was thawed in 37.0° C.±2° C. in a water bath. Once the plasma was thawed, it was quickly removed from the water bath. The plasma was adjusted to 20 mM Tris, 50 mM NaCl using a 50× dilution of 1M Tris, pH 7.5 and a 40× dilution of 2M NaCl. The plasma was mixed well and filtered using a SartoPure 300 PP2 (8 μm) sterile filter.

a. vonWillebrand Factor/Factor VIII (vWF/FVIII) Affinity Capture

A 7 cm×10.6 cm packed bed column was prepared containing 410 mL of the affinity adsorbent developed for the capture of vWF/FVIII Affinity Capture. The column was typically maintained in a Storage Solution containing 0.1 N NaOH when not in use for extended periods of time. The previously stored column was washed at a flow rate of 80 cm/hr with 3 CVs of Milli Q water until the conductivity dropped below 1 mS/cm. The column was equilibrated with 4 CVs of Equilibration (EQ) buffer composed of 20 mM Tris, 20 mM Citrate, 140 mM NaCl, pH 7.5. The filtered plasma was applied on the column. The flow-through effluent was collected when the absorbance at 280 nm reached 5% of the absorbance unit was full scale (AUFS=2).

The column was washed with 4 CV of EQ buffer while continuing to collect the column effluent until absorbance dropped down to 5% of the AUFS. The solution was mixed thoroughly but gently and then filtered through a 3/0.8 um SartoClean CA (H8) followed by a 0.45/0.22 um Sartobran P (H8) filter. The filter was post-rinsed with 500 mL of EQ buffer. The combined filtrate was mixed gently. This filtered solution constituted flow-through fraction of the vWF/FVIII capture step (vWF/FVIII-FT (flow-through)). The vWF/ FVIII was eluted with 4 CV of Elution buffer composed of 20 mM Tris, 500 mM NaCl, 3 mM CaCl$_2$, 0.01% Polysorbate 80, 30% ethylene glycol, pH 6.5. The column flow rate was set at 30 cm/hr. Collection of the eluate was initiated once the % UV increases to 2% AUFS. The eluate was continuously collected until absorbance dropped back to 2% of the AUFS. The column eluate was mixed gently and stored at −80° C. until ready for further processing. The resin was regenerated with a CIP-1 solution composed of 0.5N NaOH/1% Triton X100. The CIP-1 solution was applied to the column in the "up flow" direction at a reduced flow rate of 5 mL/min for approximately 3 CV. The resin was then washed with 2 CV of a CIP-2 solution composed of 30% iso-propanol in 0.5N NaOH at 5 mL/min. The resin was equilibrated with 3 CV of Storage Solution until the next use.

b. Plasminogen (Pg) Affinity Capture

A 5 cm×13 cm packed bed column was prepared containing 255 mL of the affinity adsorbent developed for the capture of Plasminogen. The column was typically maintained in a Storage Solution containing 0.1 N NaOH when not in use for short periods of time. The previously stored column was washed at a flow rate of 160 cm/hr with 1-2 CVs of Milli Q water until the conductivity dropped below 1 mS/cm. The column was equilibrated with 3-4 CVs of Equilibration (EQ) buffer composed of 20 mM Tris, 20 mM Citrate, 140 mM NaCl, pH 7.5. The vWF/FVIII-FT was applied from the previous capture step on the column. The flow-through effluent was collected when the absorbance at 280 nm reaches 5% of the AUFS (absorbance units full scale).

The column was washed with 2-3 CV of EQ buffer while continuing to collect the column effluent until absorbance dropped down to 5% of the AUFS. Solution was mixed gently and then filtered through a 0.22 um Sartobran filter. The filter was post-rinsed with 500 mL of EQ buffer. The combined filtrate was mixed gently. This filtered solution constituted flow-through fraction of the Plasminogen capture step (Pg-FT). The column was washed with 2 CV of Wash Buffer composed of 30 mM caprylate, in EQ, pH 7.5 followed by 2 CV of EQ buffer. The Plasminogen was eluted with 2-3 CV of Elution buffer composed of 50 mM Na phosphate, 0.5M EACA, pH 7.0. Collection of the eluate was initiated once the % UV increased to 2% AUFS. The eluate was continuously collected until absorbance dropped back to 2% of the AUFS. The column eluate was mixed gently and stored at −80° C. until ready for further processing. The resin was regenerated with a CIP-1 solution composed of 0.5N NaOH. The CIP-1 solution was applied to the column in the "up flow" direction at a reduced flow rate of 40 mL/min for approximately 4 CV. The resin was equilibrated with 3 CV of Storage Solution until the next use.

c. Fibrinogen (Fg) Affinity Capture

A10 cm×10.1 cm packed bed column was prepared containing 790 mL of the affinity adsorbent developed for the capture of Fibrinogen. The column was typically maintained in a Storage Solution containing 0.1 N NaOH when not in use for short periods of time. The previously stored column was washed at a flow rate of 60 cm/hr with 1-2 CVs of Milli Q water until the conductivity dropped below 1 mS/cm.

The column was equilibrated with 3-4 CVs of Equilibration (EQ) buffer composed of 20 mM Tris, 20 mM Citrate, 140 mM NaCl, pH 7.5. The Pg-FT was applied from the previous capture step on the column. The flow-through effluent was collected when the absorbance at 280 nm reached 5% of the AUFS (absorbance units full scale). The column was washed with 4-5 CV of EQ buffer and the column effluent was continuously collected until absorbance dropped down to 5% of the AUFS. The solution was mixed gently and then filtered through a 0.22 um Sartobran filter. The filter was post-rinsed with 500 mL of EQ buffer and the combined filtrate was mixed gently. This filtered solution constituted flow-through fraction of the Fibrinogen capture step (Fg-FT). The Fibrinogen was eluted with 4-5 CV of Elution buffer composed of 20 mM Tris, 20 mM Citrate, 140 mM NaCl, 1% Cholate, 10% propylene glycol, pH 7.5. Collection of the eluate was initiated once the % UV increased to 2% AUFS. The eluate was continuously collected until absorbance dropped back to 2% of the AUFS. The column eluate was mixed gently and stored at −80° C. until ready for further processing. The resin was regenerated with a CIP-1 solution composed of 1.0N NaOH. The CIP-1 solution was applied to the column in the "up flow" direction at a reduced flow rate of 80 mL/min for approximately 4 CV. The resin was equilibrated with 3 CV of Storage Solution until the next use.

d. Immunoglobulin G (IgG) Affinity Capture

The load was prepared by adding 1/10 volume of load adjustment buffer (300 mM caprylate in EQ) to the Fg-FT and mixed well. A 14 cm×12.2 cm packed bed column was prepared containing 1880 mL of the affinity adsorbent developed for the capture of IgG. The column was typically maintained in a Storage Solution containing 0.1 N NaOH when not in use for short periods of time. The previously stored column was washed at a flow rate of 73 cm/hr with 2 CVs of Milli Q water until the conductivity dropped below 1 mS/cm. The column was equilibrated with 2 CV of Wash buffer composed of 20 mM Tris, 20 mM Citrate, 1 M NaCl, pH 7.5 followed by 3-5 CV of IgG Equilibration buffer composed of 30 mM caprylate, 20 mM Tris, 20 mM Citrate, 140 mM NaCl, pH 7.5. The Fg-FT was applied from the previous capture step on the column. The flow-through effluent was collected when the absorbance at 280 nm reached 5% of the AUFS (absorbance units full scale).

The column was washed with 4-5 CV of Wash buffer continuing to collect the column effluent until absorbance dropped down to 5% of the AUFS. The solution was mixed gently and then filtered through a 0.22 um Sartobran filter. The filter was post-rinsed with 500 mL of EQ buffer and the combined filtrate was combined gently. This filtered solution constituted flow-through fraction of the IgG capture step (IgG-FT). Prior to elution of the IgG, the column was conditioned with 1 CV of Pre-Elution buffer composed of 50 mM citrate, pH 6.0. Elute the IgG with 4 CV of Elution buffer composed of 50 mM citrate, pH 3.0. Collection of the eluate was initiated once the % UV increased to 2% AUFS. Collecting the eluate was continued until absorbance dropped back to 2% of the AUFS. The column eluate was mixed gently and the pH was adjusted above pH 7.0 with a sufficient volume of 1M Tris Base and then stored at −80° C. until ready for further processing. The resin was regenerated with a CIP-1 solution composed of 1.0N NaOH. The CIP-1 solution was applied to the column in the "up flow" direction at a reduced flow rate of 170 mL/min for approximately 4 CV followed by 3 CV of Milli-Q water in the down-flow direction. The resin was equilibrated with 3 CV of Storage Solution until the next use.

e. Ultrafiltration/Diafiltration

Filtration was conducted to concentrate the IgG-FT product until the target volume of approximately 1.5-2 L was reached. Diafiltration was conducted against 6 volumes of EQ buffer with a filter inlet pressure (P1) of 18±1 psi and a TMP of 15±1 psi. The permeate was sampled for pH and conductivity measurements at the beginning of diafiltration and at approximately every retentate volume of diafiltration to monitor when diafiltration was complete.

f. Albumin (HSA) Affinity Capture

A 20 cm×17.8 cm packed bed column was prepared containing 5600 mL of the affinity adsorbent developed for the capture of Albumin. The column was typically maintained in a Storage Solution containing 0.1 N NaOH when not in use for short periods of time. The previously stored column was washed at a flow rate of 86 cm/hr with 2 CVs of Milli Q water until the conductivity dropped below 1 mS/cm. The column was equilibrated with 3-4 CV of EQ buffer. The UF/DF retentate was applied from the previous step on the column. The flow-through effluent was collected when the absorbance at 280 nm reached 5% of the AUFS (absorbance units full scale).

The column was washed with 2-3 CV of EQ buffer continuing to collect the column effluent until absorbance dropped down to 5% of the AUFS. Solution was mixed gently. This filtered solution constituted flow-through fraction of the Albumin capture step (HSA-FT). Prior to elution of the Albumin the column was conditioned with 2 CV of Pre-Elution buffer composed of 50 mM Citrate, 300 mM NaCl, pH 7.5. The Albumin was eluted with 2-3 CV of Elution buffer composed of 50 mM Na Citrate, 50 mM Na Caprylate, pH 6.2. Collection of the eluate was initiated once the % UV increased to 2% AUFS. The eluate was continuously collected until absorbance dropped back to 2% of the AUFS. The column eluate was mixed gently and then stored at −80° C. until ready for further processing. The resin was regenerated with a CIP-1 solution composed of 1.0N NaOH. The CIP-1 solution was applied to the column in the "up flow" direction at a reduced flow rate of 400 mL/min for approximately 4 CV followed by 3 CV of Milli-Q water in the down-flow direction. The resin was equilibrated with 3 CV of Storage Solution until the next use.

g. Concentrating HSA Flow-Through

Connect the HSA-FT bag containing the rest of the sample to the tubing inlet on the product reservoir. Start the pump at a "Constant Flow Rate" of 1300 mL/min on the Slice 200 system. Set the pressure at the filter outlet (P2) to 13±1 psi. This should result in a filter inlet pressure (P1) of 18±1 psi and a TMP of 15±1 psi. While concentrating the product, additional HSA-FT was continuously fed into the system reservoir. Concentrating the HSA-FT was continued until the target volume of approximately 1.5-2 L was reached. Re-circulating was continued for approximately 1 minute without pressure or filtration through the membrane before harvesting the UF product from the filter system. About 500-1000 mL of equilibration buffer was added to the reservoir to rinse the filter system. Re-circulating began slowly to avoid "foaming" the system rinse for approximately 3 to 5 minutes, with no filtration or pressure. The UF-Product was combined, rinsed and stored at −80° C. The HAS-FT concentrate was considered an appropriate starting material for the purification of A1PI.

Results

TABLE 10

| Key attributes for vWF/FVIII capture | | |
|---|---|---|
| Sample | Mean | SD |
| Load: | | |
| vWF Concentration (ug/mL) | 10.88 | 1.34 |
| FVIII Concentration (ng/mL) | 78.5 | 6.7 |
| Volume (L) | 4061 | 116 |
| pH | 7.73 | 0.06 |
| Conductivity (mS/cm) | 15.6 | 0.5 |

TABLE 10-continued

Key attributes for vWF/FVIII capture

| Sample | Mean | SD |
|---|---|---|
| Flow-Through: | | |
| vWF Concentration (ug/mL) | 1.09 | 0.39 |
| FVIII Concentration (ng/mL) | 12.87 | 2.23 |
| Volume (L) | 5597.1 | 87.5 |
| pH | 7.6 | 0.13 |
| Conductivity (mS/cm) | 17 | 0.577 |
| Elution: | | |
| vWF Concentration (ug/mL) | 26.8 | 5.48 |
| FVIII Concentration (ng/mL) | 298.5 | 72.1 |
| Volume (L) | 697.1 | 121.6 |
| pH | 8.47 | 0.56 |
| Conductivity (mS/cm) | 22.64 | 0.69 |

TABLE 11

Key attributes for Plasminogen capture

| Sample | Mean | SD |
|---|---|---|
| Load: | | |
| Titer (g/L) | 0.081 | 0.003 |
| Vol (L) | 5859 | 145 |
| pH | 7.75 | 0.09 |
| Conductivity (mS/cm) | 17.32 | 1.19 |
| Flow-Through: | | |
| Titer (g/L) | 0.005 | 0.005 |
| Vol (L) | 6346 | 269 |
| pH | 7.71 | 0.07 |
| Conductivity (mS/cm) | 17.50 | 0.76 |
| Elution: | | |
| Titer (g/L) | 1.488 | 0.127 |
| Vol (L) | 236.3 | 17.5 |
| pH | 7.27 | 0.06 |
| Conductivity (mS/cm) | 14.71 | 3.68 |

TABLE 12

Key attributes for Fibrinogen capture

| Sample | Mean | SD |
|---|---|---|
| Load: | | |
| Titer (g/L) | 1.43 | 0.06 |
| Vol (L) | 6716 | 181 |
| pH | 7.72 | 0.04 |
| Conductivity (mS/cm) | 16.57 | 0.84 |
| Flow-Through: | | |
| Titer (g/L) | 0.0323 | 0.005 |
| Vol (L) | 9507 | 231 |
| pH | 7.55 | 0.08 |
| Conductivity (mS/cm) | 17.00 | 0.96 |
| Elution: | | |
| Titer (g/L) | 3.433 | 0.253 |
| Vol (L) | 2539 | 227 |
| pH | 7.55 | 0.08 |
| Conductivity (mS/cm) | 14.00 | 1.41 |

TABLE 13

Key attributes for IgG Capture

| Sample | Mean | SD |
|---|---|---|
| Load: | | |
| Titer (g/L) | 2.251 | 0.259 |
| Vol (L) | 10429 | 267 |
| pH | 7.54 | 0.25 |
| Conductivity (mS/cm) | 18.52 | 0.92 |
| Flow-Through: | | |
| Titer (g/L) | 0.015 | 0.003 |
| Vol (L) | 12620 | 876 |
| pH | 7.61 | 0.09 |
| Conductivity (mS/cm) | 32.17 | 6.05 |
| Elution: | | |
| Titer (g/L) | 3.762 | .481 |
| Vol (L) | 6086 | 741 |
| pH | 7.64 | 0.64 |
| Conductivity (mS/cm) | 10.64 | 6.55 |

TABLE 14

Key attributes for HSA capture

| Sample | Mean | SD |
|---|---|---|
| Load: | | |
| Titer (g/L) | 28.55 | 1.84 |
| Vol (mL) | 3814 | 211 |
| pH | 7.45 | .08 |
| Conductivity (mS/cm) | 17.21 | 1.75 |
| Flow-Through: | | |
| Titer (g/L) | .047 | .003 |
| Vol (mL) | 10463 | 2015 |
| pH | 7.39 | 0.13 |
| Conductivity (mS/cm) | 17.42 | 1.79 |
| Elution: | | |
| Titer (g/L) | 18.27 | 2.47 |
| Vol (mL) | 5906 | 650 |
| pH | 6.76 | .04 |
| Conductivity (mS/cm) | 22.00 | 3.78 |

TABLE 15

Process Yields for target proteins

| Protein | Assay Type | Mean Yield | Std. Dev. |
|---|---|---|---|
| Von Willebrand Factor | ELISA | 43% | 12% |
| Factor VIII | ELISA | 65% | 11% |
| Plasminogen | Nephelometry | 72% | 6% |
| Fibrinogen | Nephelometry | 79% | 6% |
| IgG | Nephelometry | 87% | 7% |
| HAS | Nephelometry | 88% | 8% |
| A1PI | Nephelometry | 90% | 6% |

Example 3

Evaluation and Selection of Plasma Buffering System for Use in Linear Cascade Process This experiment was performed in order to determine the optimum buffering system for the linear cascade sequence plasma protein purification scheme. It was observed that during the IgG column load the pH climbed to 2 units above that of the plasma (pH ~7.5). A shift in pH during IgG loading was observed several times and appeared to be dependent on the degree of protein depletion of the load. This suggested that certain plasma proteins have buffering capacity, and removal of these proteins from the load solution may increase the likelihood of a shift in the pH. A buffering system for the plasma was needed to preserve the protein concentration and activity in the plasma. The buffering system had to be such that the pH remained in an acceptable range of about 7.5±0.4 throughout the process.

To ensure that the pH shift would not occur in the subsequent run, the plasma load for the subsequent operation was buffered using a stock solution of 1 M Tris at pH 7.5. This stock buffer was created using two separate stocks, 1 M Tris Base and 1 M Tris HCl. These buffers were titrated with each other to pH 7.5. The stock buffer was then diluted 1:20 in plasma before filtration. The final prepared load contained 50 mM Tris adjusted plasma, filtered with a 0.45/0.2 μm filter.

An alternative buffering system was sought due to the relatively high projected costs of 50 mM Tris buffer at manufacturing scale. Several experiments were performed on small aliquots of plasma buffered with bicarbonate, phosphate, and Tris at pH 7.5. These experiments were carried out over the course of several days to simulate the multi-day LCS. Aliquots of the same plasma pool were buffered and left to incubate at room temperature (RT) for several days. Samples of each were analyzed for activity and protein concentration. Presented in Table 16 are the yields per incubation step when the plasma is buffered with each system. Plasma buffered with 50 mM Tris was performed several times as the benchmark for comparison.

TABLE 16

Summary of Preliminary Plasma Buffering Studies.
Yields after incubation at RT

| | FG | FG (act) | FXIII (act) | IgG | A1PI | A1PI (ac) |
|---|---|---|---|---|---|---|
| In plasma buffered with 50 mM Tris, t = 24 h | 100% (n = 2) | 99% (n = 2) | 100% (n = 2) | 95% (n = 2) | 101% (n = 2) | 98% (n = 2) |
| In plasma buffered with 20 mM Sodium Bicarbonate, t = 24 | 113.00% | 99.00% | 104.00% | 108.00% | 97.00% | 84.00% |
| In plasma buffered with 50 mM Sodium Bicarbonate, t = 24 | 98.00% | 114.00% | 115.00% | 102.00% | 97.00% | 97.00% |
| In plasma buffered with 50 mM Sodium Phosphate, t = 24 h | 96.00% | 95.00% | 95.00% | 99.00% | 97.00% | 103.00% |
| In plasma buffered with 50 mM Sodium Phosphate, t = 48 h (yield is presented as from t = 24 to t = 48 hr) | 109.00% | 99.00% | 100.00% | 100.00% | 100.00% | 97.00% |

This buffering system was used for the determination of linear cascade sequence (LCS) experiments 1-7. 50 mM Tris buffer was used in the plasma and running buffer throughout the process. No pH problems during column load were observed while 50 mM Tris, pH 7.5 was in use. Table 15 summarizes the step yields of LCS purifications performed using 50 mM Tris, pH 7.5 as the plasma buffer.

TABLE 15

Percentage Step Yields of Target Proteins through
the LCS buffered with 50 mM Tris, pH 7.5.

| 50 mM Tris Buffer | Fg | FXIII | IgG | A1PI | A1PI (activity) |
|---|---|---|---|---|---|
| Pg | 95 ± 2.7 (n = 6) | 91.3 ± 7.4 (n = 4) | 98 ± 3.7 (n = 7) | 100 ± 13 (n = 7) | 100.3 ± 15.8 (n = 5) |
| Fg | | | 86.6 ± 8 (n = 7) | 95.5 ± 5.3 (n = 7) | 107.7 ± 9.1 (n = 5) |
| IgG | | | | 87.8 ± 13.3 (n = 7) | 96.7 ± 7.4 (n = 5) |
| HSA | | | | 96.1 ± 19.5 (n = 7) | 98.5 ± 23 (n = 4) |

The results indicated that there was no greater loss of protein or activity with various buffers tested when compared to the control, water. None of the target proteins were affected adversely by the addition of a buffering agent to the plasma. Each buffering scheme was then tested in a cascade study to determine the optimum buffering conditions.

A buffering system of 10 mM sodium phosphate was evaluated during the LCS experiments. During the plasma load preparation, a stock solution of 0.2 M Na phosphate was diluted to 10 mM Na phosphate with a 20-fold dilution of the stock buffer with plasma. The 10 mM phosphate buffered plasma was filtered to 0.2 μm before its use in the linear cascade study. During the trial of this buffering scheme, the protein activity was noticeably lower for target proteins and other factors that were indicative to protein activity. Table 17 below summarizes the step yields of several LCS runs using 10 mM phosphate buffer.

TABLE 17

Percentage Step Yields of Target Proteins through the LCS buffered with 10 mM Sodium Phosphate, pH 7.5.

| 10 mM Phosphate Buffer | Fg | FXIII | IgG | A1PI | A1PI (activity) |
|---|---|---|---|---|---|
| Pg | 94 ± 3.5 (n = 6) | 80.4 ± 7.4 (n = 5) | 96.9 ± 5.1 (n = 6) | 97.3 ± 6.2 (n = 6) | 95.5 ± 7.8 (n = 6) |
| Fg | | | 78.2 ± 5.5 (n = 6) | 90.9 ± 8 (n = 6) | 89.5 ± 25 (n = 5) |
| IgG | | | | 87.2 ± 7.4 (n = 5) | 80 ± 21 (n = 4) |
| HAS | | | | 94 ± 8.1 (n = 3) | ND |

While Tris buffered plasma at 50 mM had been successful in avoiding pH swings, a more cost effective means of buffering plasma was needed. As a result, 20 mM Tris, pH 7.5 was used for the LCS. Plasma was adjusted to 20 mM Tris at pH 7.5 by a 50-fold dilution of 1 M Tris, pH 7.5. This stock buffer was made as above, titrating tris base with Tris HCl. Table 18 shows that performance of LCS runs by using plasma titrated to 20 mM Tris is comparable to that of 50 mM Tris buffer as described above in terms of target protein recoveries, buffering capacity, and load stability.

TABLE 18

Percentage Step Yields of Target Proteins through the LCS buffered with 20 mM Tris, pH 7.5.

| 20 mM Tris Buffer | Fg | FXIII | IgG | A1PI | A1PI (activity) |
|---|---|---|---|---|---|
| Pg | 97 ± 5.6 (n = 8) | 88.7 ± 17 (n = 8) | 103.2 ± 13.4 (n = 8) | 99.3 ± 8 (n = 8) | 104.3 ± 13 (n = 4) |
| Fg | | | 86.4 ± 7.1 (n = 8) | 90 ± 6.2 (n = 8) | 90 ± 12 (n = 4) |
| IgG | | | | 87.1 ± 3.2 (n = 7) | 91.7 ± 7 (n = 3) |
| HSA | | | | 95 ± 6.8 (n = 6) | 88.2 ± 19 (n = 3) |

TABLE 19

HSA Step Yields Through the LCS Using Different Buffer Systems.

| HSA with various Buffers | Tris 50 mM | Phosphate 10 mM | Tris 20 mM |
|---|---|---|---|
| Pg | 97.4 ± 3.9 (n = 6) | 95.5 ± 4.3 (n = 6) | 95.6 ± 8.1 (n = 8) |
| Fg | 95 ± 5.7 (n = 6) | 94.8 ± 9.2 (n = 6) | 97.8 ± 4.6 (n = 7) |
| IgG | 84 ± 9.8 (n = 6) | 79.1 ± 18.3 (n = 5) | 86.4 ± 2.1 (n = 7) |
| Overall Yield | 77.4 | 71.6 | 80.1 |

Table 19 represents the results of a comparison between the evaluated buffering systems in terms of HSA step yields through the LCS. Overall, the step recoveries for HSA capture among three buffers tested were comparable to each other, except with 10 mM phosphate, a lower yield for HSA was evidenced with IgG capture step. Also, IgG, a higher value target protein, had a lower recovery during fibrinogen capture step when 10 mM phosphate buffer was applied. All values were percentage yields indicated for each capture step. The data were gathered from 0.5 L runs, step recoveries were calculated solely based on the amount of albumin presented in the load and the flow-through.

It was concluded that a buffer containing 50 mM Tris was an effective plasma buffer that may be too costly as the process is scaled up to manufacturing. Several alternatives to Tris were evaluated and subjected to full LCS runs. These alternatives were judged based upon buffering capacity, ease of use, cost, and conservation of protein concentration and activity. It was found that a reduced molarity Tris (20 mM) at pH 7.5 was effective as a plasma buffer.

The present invention may be embodied in other specific forms without departing from the spirit or essential attributes thereof and, accordingly, reference should be made to the appended claims, rather than to the foregoing specification, as indicating the scope of the invention.

Sequence Listings
SEQ ID NO: 1
Amino acid
ARQFDF

What is claimed is:

1. A method of sequential protein isolation and purification comprising:
   (i) providing a plasma sample,
   (ii) providing a plurality of ligands each of which binds specifically to a target protein in the plasma sample, wherein each of the plurality of ligands is optionally attached to a support to form a plurality of ligand-support complexes,
   (iii) contacting the plurality of ligands or ligand-support complexes in a predetermined order with the plasma sample to allow each ligand or ligand-support complex to bind its respective target protein from the plasma sample, wherein the predetermined order of contacting the plurality of ligands or ligand-support complexes with the plasma sample results in the binding of plasminogen before fibrinogen and fibrinogen before IgG and IgG before albumin, and wherein the plasma sample is not processed through any pre-conditioning step that includes alcohol precipitation, cryoprecipitation, removal of lipids and/or lipid proteins, euglobulin precipitation, or a combination thereof prior to said contacting the plurality of ligands or ligand-support complexes,
   (iv) eluting the respective target proteins bound to each of the plurality of ligands or ligand-support complexes, and
   (v) isolating the respective target proteins.

2. The method of claim 1, wherein the activity of paraoxonase is retained in the plasma sample during the protein isolation.

3. The method of claim 1, wherein vWF/FVIII is isolated from the plasma prior to said contacting the plasma sample with a ligand or ligand-support complex specific for plasminogen.

4. The method of claim 1, wherein apolipoprotein A1 is isolated from the plasma prior to said contacting the plasma sample with a ligand or ligand-support complex specific for IgG.

5. The method of claim 1, wherein alpha-1 proteinase inhibitor is isolated from the plasma after said contacting the plasma sample with a ligand or ligand-support complex specific for albumin.

6. The method of claim 1, wherein the ligand comprises a peptide, polypeptide, peptidomimetic, small molecule, dye, triazine containing compound, antibody or antigen-binding fragment, nucleic acid-based molecule, non-polypeptide or nucleotide-based molecule, carbohydrate, carbohydrate mimetics, lipids, inorganic material, inhibitor, substrate or any combination thereof.

7. The method of claim 6, wherein the ligands comprise peptides consisting essentially of about 1 to about 15 amino acids.

8. The method of claim 1, wherein the support comprises a synthetic material, a natural material, or both.

9. The method of claim 1, wherein the support comprises agarose, polyacrylamide, dextran, cellulose, polysaccharide, nitrocellulose, silica, alumina, aluminum oxide, titania, titanium oxide, zirconia, styrene, polyvinyldifluoride nylon, copolymer of styrene and divinylbenzene, polymethacrylate ester, derivatized azlactone polymer or copolymer, glass, cellulose, agarose, derivatives of any of the foregoing, and combinations of any of the foregoing.

10. The method of claim 1, wherein the support is a resin bead.

11. The method of claim 1 further comprising treating the plasma sample with a buffering agent prior to the step of contacting to conserve concentration and activity of one or more target agents in the plasma sample.

12. The method of claim 1 further comprising treating the plasma sample by diluting, adjusting pH, ionic strength or polarity, temperature, or adding a soluble agent prior to the step of contacting.

13. The method of claim 1 further comprising filtering the plasma sample through a filter prior to the step of contacting.

14. The method of claim 1 wherein the overall yield of albumin removed from the plasma is at least about 71%.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: peptide ligand

<400> SEQUENCE: 1

Ala Arg Gln Phe Asp Phe
1               5